United States Patent [19]
Chen et al.

[11] Patent Number: 6,105,191
[45] Date of Patent: Aug. 22, 2000

[54] TOOTHBRUSH WITH INTER- GINGIVA-SULCUS SCRAPING BRISTLES

[76] Inventors: Kuo-Shen Chen, 4F-1, No. 16, Ln. 541, Sung-Shan Rd., Taipei, Taiwan; Tsehua Chen, 20261 Herriman Ave., Saratoga, Calif. 95070-4905

[21] Appl. No.: 09/175,839

[22] Filed: Oct. 19, 1998

[51] Int. Cl.[7] ............................. A46B 09/04; A46B 13/00
[52] U.S. Cl. .......................... 15/22.1; 15/22.2; 15/167.2; 15/111
[58] Field of Search .................................. 15/22.1, 22.2, 15/22.4, 111, 167.1, 167.2

[56] References Cited

U.S. PATENT DOCUMENTS

| | | | |
|---|---|---|---|
| 1,852,480 | 4/1932 | Ruetz | 15/111 |
| 5,068,939 | 12/1991 | Holland | 15/22.1 |
| 5,088,145 | 2/1992 | Whitefield | 15/22.2 |
| 5,715,556 | 2/1998 | Chung | 15/22.1 |
| 6,018,840 | 2/2000 | Guay et al. | 15/167.1 |

FOREIGN PATENT DOCUMENTS 3116189  12/1982  Germany .
1783978  12/1992  Russian Federation .

*Primary Examiner*—Robert J. Warden, Sr.
*Assistant Examiner*—Andrea Aldag
*Attorney, Agent, or Firm*—W. Wayne Liauh

[57] ABSTRACT

A toothbrush with scraping bristles has a plural number of bristle clusters crisscrossly mounted on a block head. The tip of the bristle clusters has a contour mating with dental area. In the block head, there are provided with a scraping bristle stem which has a plural number of movable scraping bristles normally extendable out of the block head for moving to and fro in the gingiva sulcus to scrape off tartars formed on teeth surface. A plural number of spaced and triangle scraping flakes may be disposed on each scraping bristle to enhance the effect of scraping tartars and dental plaque formed in the inter-gingiva-sulcus. The toothbrush may be used manually or be driven electrically.

10 Claims, 10 Drawing Sheets

TOOTHBRUSH WITH INTER-GINGIVA-SULCUS SCRAPING BRISTLES

BACKGROUND OF THE INVENTION

1. Field of the Invention

This invention relates to a toothbrush and particularly to a toothbrush having bristles mating with dental arch and having inter-gingiva sulcus scraping bristles that are able to pierce into inter-gingiva sulcus manually or electrically for removing tartars formed therein.

2. Description of the Prior Art

Conventional toothbrush usually has clusters of bristles fixedly disposed on a block head of the toothbrush. The bristles are shaped in a fixed form. Variation mainly has been focused on shape and angle of block handle, length and material selection of the bristles, etc. A conventional toothbrush generally can only clean outer surface of teeth (as shown in FIG. 1). The bristle A usually cannot move into the interdental area. Moreover, some people do not develop correct way of brushing teeth. Hence most people have some degree of tartar formed on their teeth. Enamel of teeth is often damaged to various degree resulting from poor brushing. Some people even have gum bleeding or affection once in a while. The wrong way of brushing teeth also can cause a toothbrush deformed and become not effective easily.

SUMMARY OF THE INVENTION

In view of the problems set forth above, it is therefore an object of this invention to provide a toothbrush which has bristles mating with dental arch. The bristles are further being laid out crisscrossly so that when the toothbrush of this invention may make close contact with teeth without gap. Moreover this invention provides scraping stems in the block head of the toothbrush. Each scraping stem has a plural number of scraping bristles spaced according to interdental area and being formed to the depth of inter-gingiva-sulcus. Therefore when the toothbrush of this invention is placed against teeth with the bristles mating against dental arch, the scraping bristles may be pierced into the inter-gingiva-sulcus and be moved to and fro therein manually or electrically for removing tartars thoroughly.

It is another object of this invention to provide a toothbrush that has sleeves located on the block head to surround the scraping bristles so that the scraping bristles can maintain normal position against the block head of the toothbrush, thus, the scraping bristles may perform scraping function more effectively.

It is a further object of this invention to provide a toothbrush with scraping bristles that has triangle scrape flakes formed on each scraping bristle. The bottom scrape flake of each scraping bristle is water resistant. The scrape flakes are elastic and may be squeezed and extended when moving in the inter-gingiva-sulcus such that the angle of the scrape flake may scrape root and top of inter-gingiva-sulcus thoroughly for removing tartars and dental plague formed on the teeth. It thus provide more effective teeth cleaning function than convention dental floss. And such cleaning job may be done immediately after toothbrushing.

BRIEF DESCRIPTION OF THE DRAWINGS

The invention, as well as its many advantages, may be further understood by the following detailed description and drawings in which.

DETAILED DESCRIPTION OF THE PREFERRED EMBODIMENT

Figure 1:
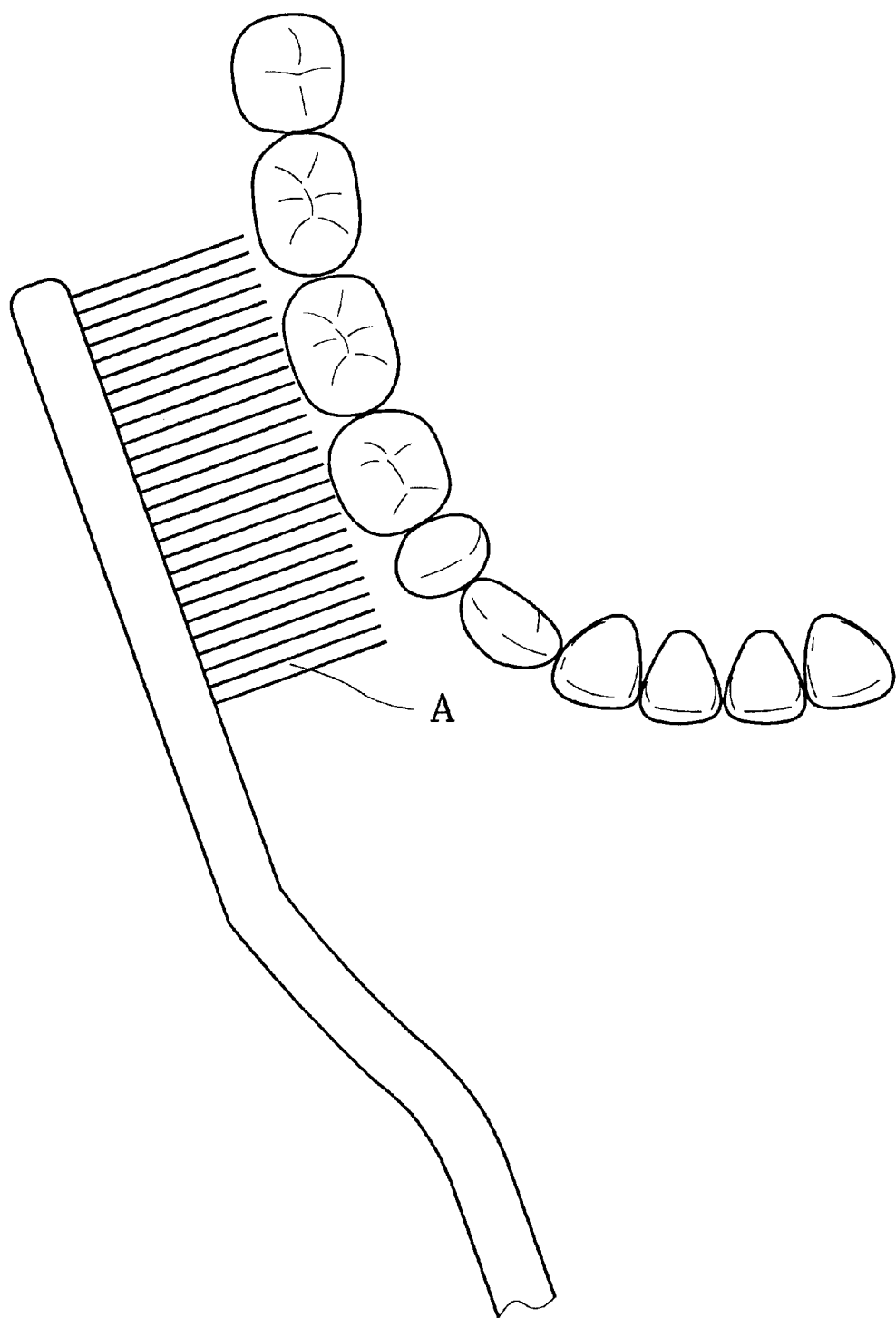
FIG. 1 is a pictorial view of a conventional toothbrush in use.
Figure 2:
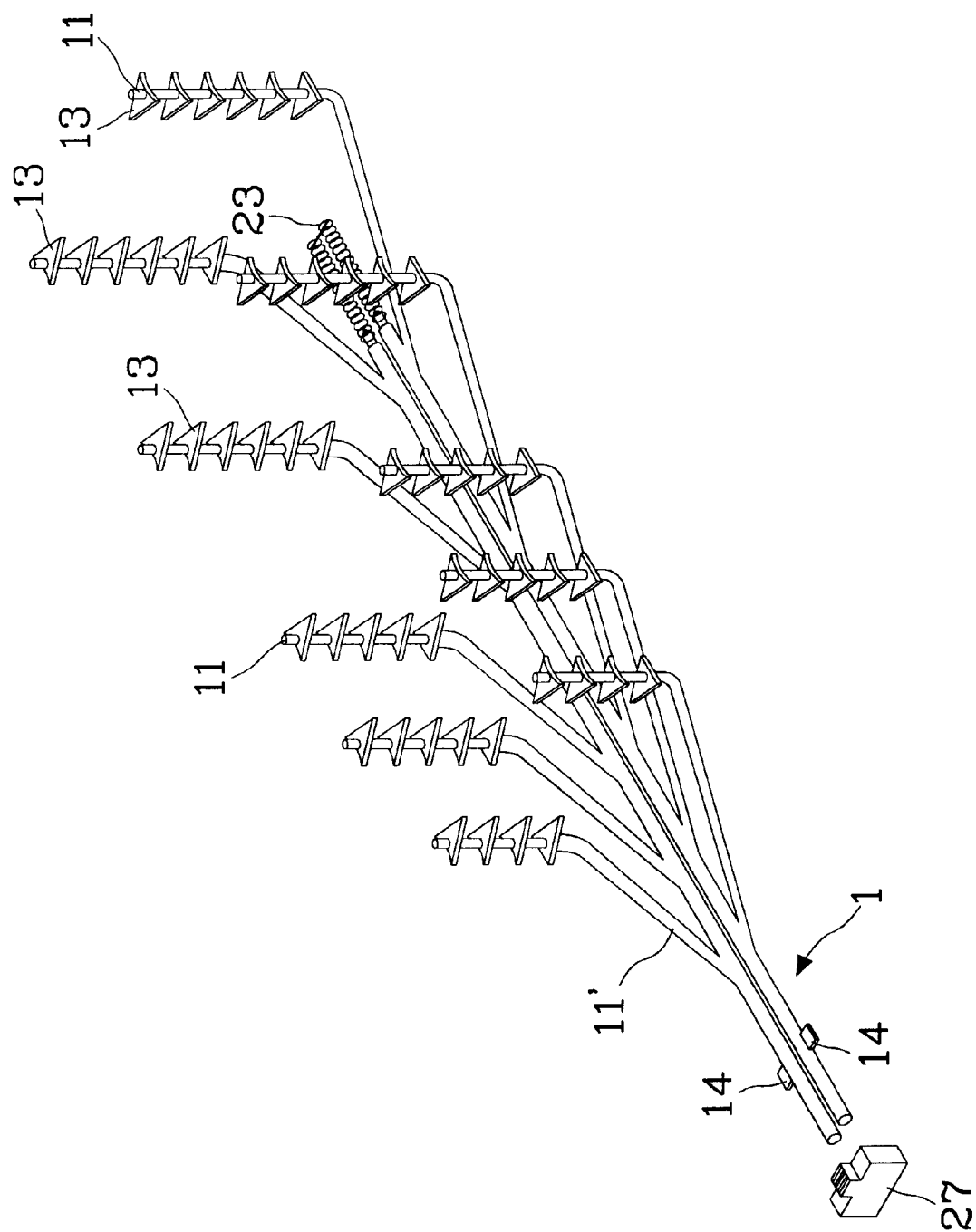
FIG. 2 is a perspective view of the gingiva sulcus scraping bristle stem of this invention.
Figure 3:
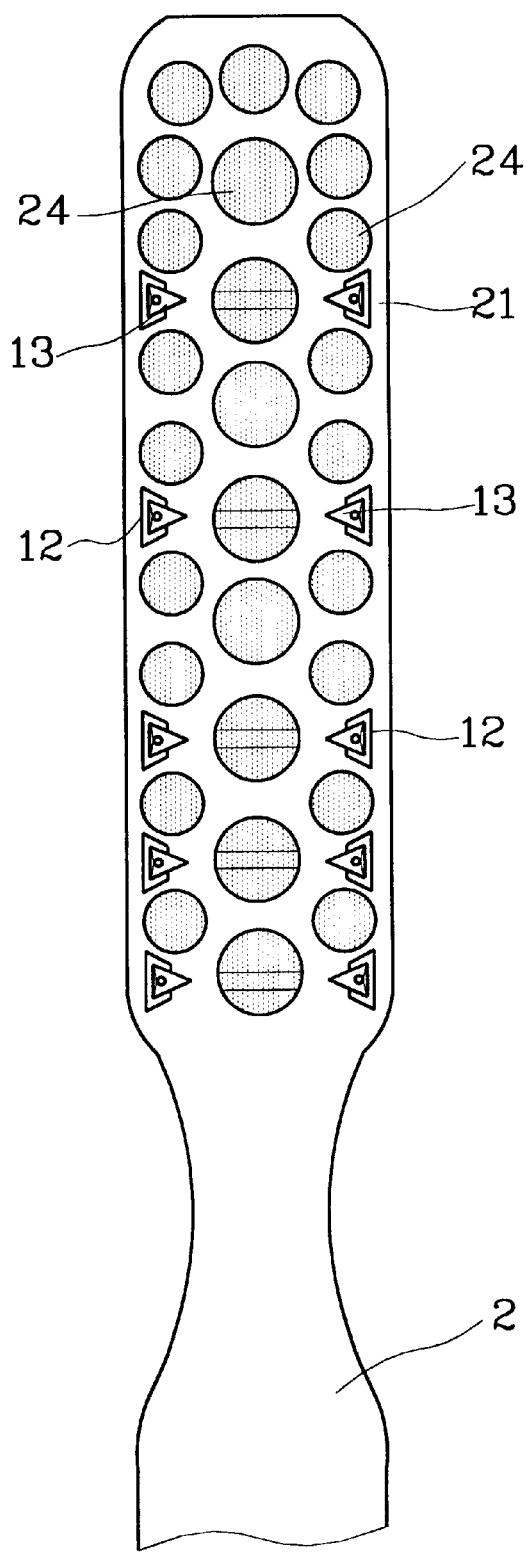
FIG. 3A is a top view of a block head of this invention.
FIG. 3B is a side view of this invention in use.
Figure 3:
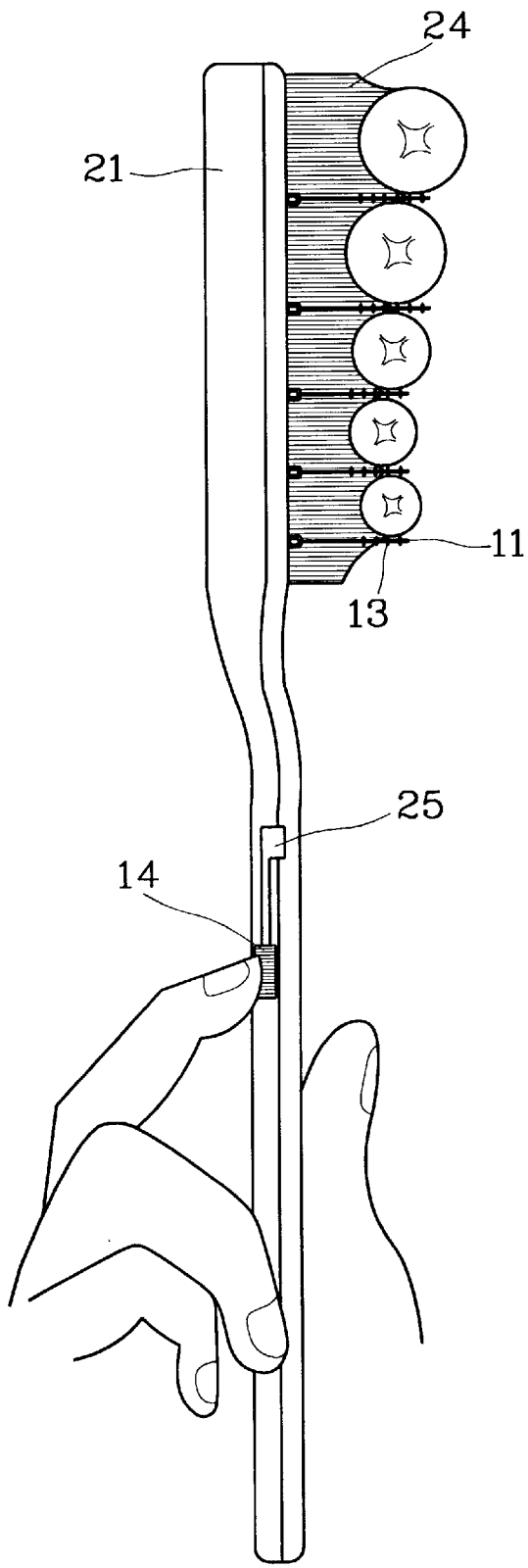

Referring to FIGS. 2, 3A, and 3B the toothbrush according to this invention includes bristles 24 disposed on a block head and with their tips formed according to dental arch (shown in FIG. 3B). The bristles 24 further are crisscross laid out so that they can effectively access to the interdental area (shown in FIG. 3A). There are a pair of scraping bristle stems 1 movably located in the block head. Each scraping bristle stem includes a plural number of spaced scraping bristles 11 respectively extending from the bristle branches 11 which are mating with the interdental area. Each scraping bristle 11 can pierce through a gingiva sulcus to scrape tartars formed on the surface of the teeth. There is a sleeve 12 located around the exit where the scraping bristle 11 leaving the block head to keep the scraping bristle 11 maintaining normal position against the surface of the block head so that when the bristles 24 making contact with dental arch, the scraping bristle 11 may move reciprocally to and fro, manually or electrically, in the gingiva sulcus to scrape tartars thoroughly. Furthermore each scraping bristle 11 may be provided with a plural number of triangle scrape flakes 13. The flake at the bottom is water resistant. The scrape flakes are made by elastic material such that when the scraping bristle 11 moves reciprocally in the gingiva sulcus, the scrape flakes will be squeezed and expand again alternately multiple of times. This multiple scraping function has more effective scraping effect to remove tartars than conventional dental floss.

Figure 4:
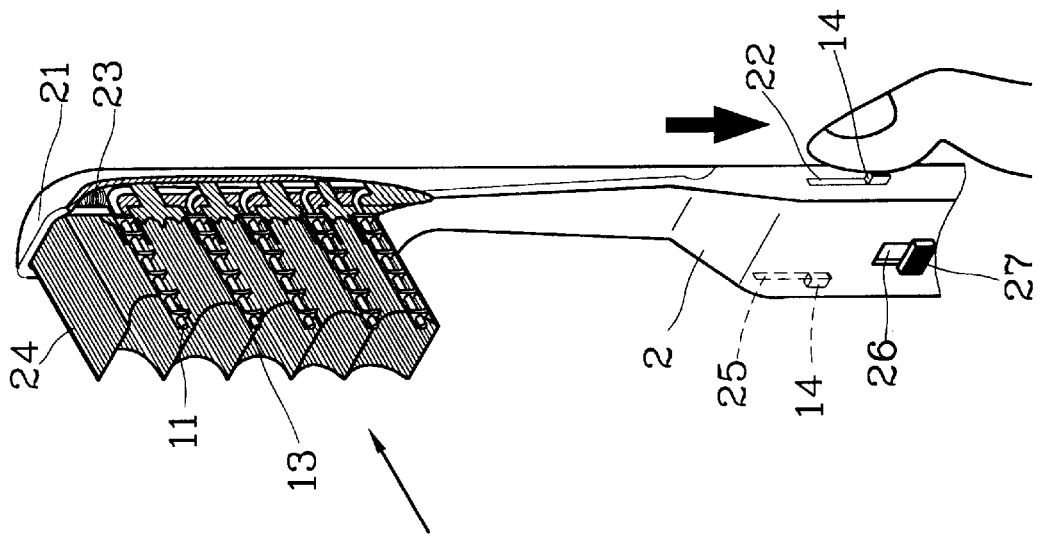
FIGS. 4A and 4B are perspective views of this invention in use, with manually driven scraping bristles.
Figure 4:
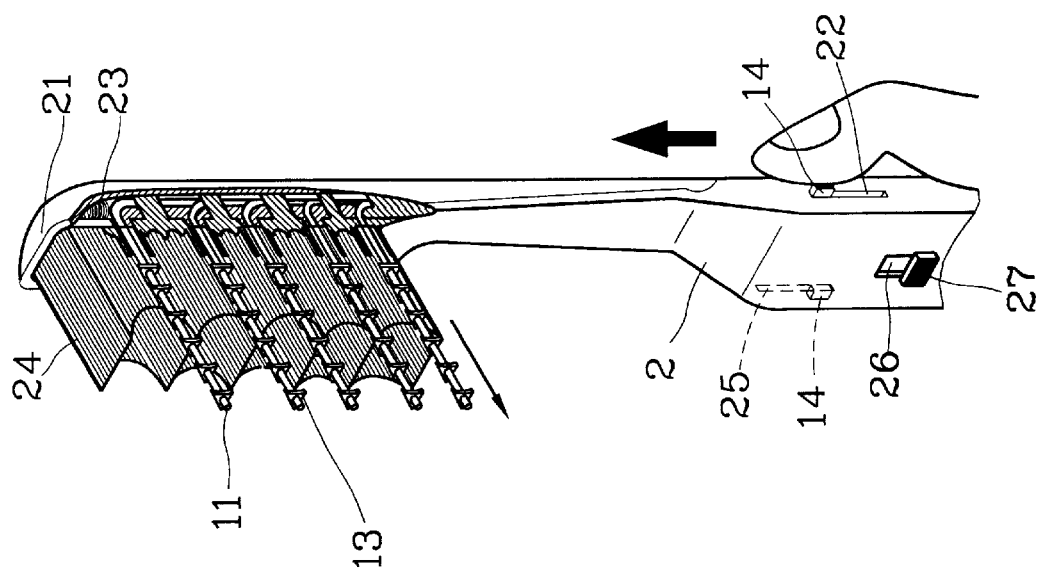

FIGS. 4A and 4B show this invention in use manually. The block handle 2 of the toothbrush has a first slot 22 and a second slot 25 located respectively on two lateral sides thereof. Each scraping bristle stem 1 has a side button 14 (shown in FIG. 2) slidably engageable with the slots 22 and 25. At the end of the scraping bristle stem 1, there is a master button 27 movable in a third slot 26 formed in the block handle 2 for moving two scraping bristle stems at the same time. At another end in the block head 21 and opposite to the master button 27, there is provided with a pair of elastic members 23, preferably coil springs, engageable respectively with another end of the scraping bristle stem 1 for pressing the scraping stem 1 at a retraction position so that a user may use the bristles 24 to clean teeth like a conventional toothbrush when the scraping bristles are not in use. When in use, pushing the side button 14 toward the block head, one set of scraping bristle 11 will be moved outward from the sleeve 12 and extended out of the bristle 24 for scraping in the gingiva sulcus (FIG. 4A). As another end of the bristle stem is pressed against the elastic members 23, once the thumb or finger releases the side button 14, the scraping bristle stem 1 will be pushed backward by the elastic members 23. Hence a reciprocal motion may be produced by simply moving the side button 14 forward then release. The side button 14 enables a user to move one scraping bristle stem 1 at a time. In case to move two scraping bristle stems 1 is desired, the user may push the master button 27 forward in the third slot 26, then all scraping brushes will be pushed out of the block head to facilitate cleaning of the scraping brushes.

Figure 5:
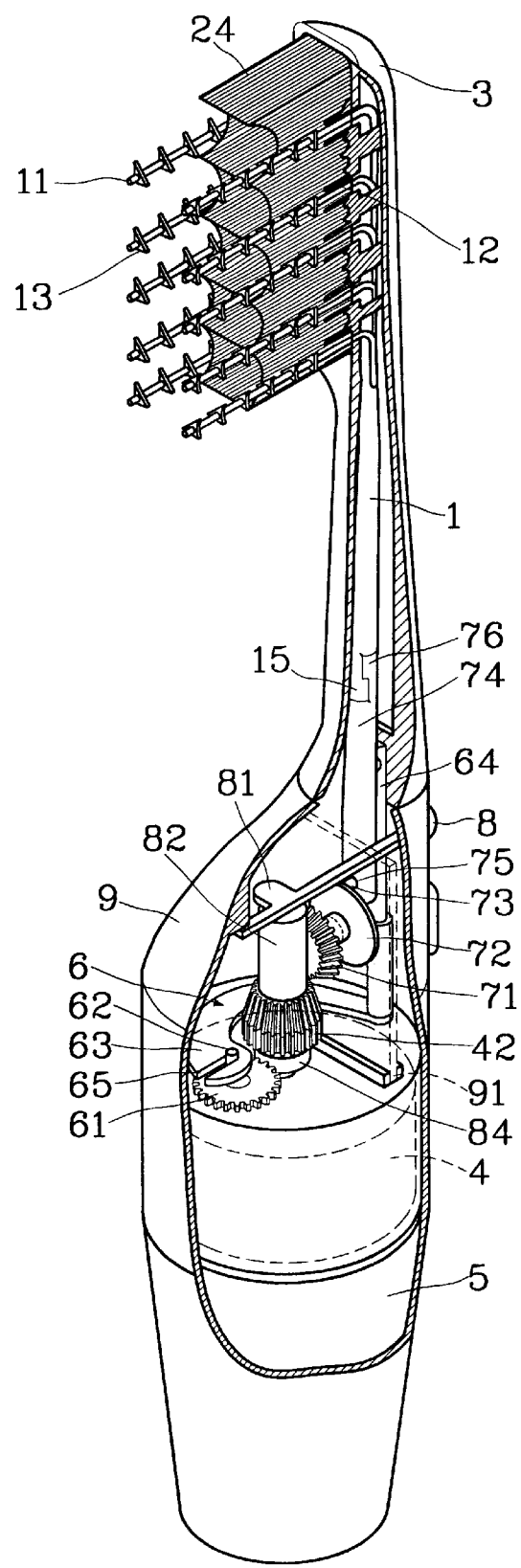
FIG. 5 is a perspective view, partly cutaway, of another embodiment of this invention, with electrical driven brush and scraping bristles.
Figure 6A:
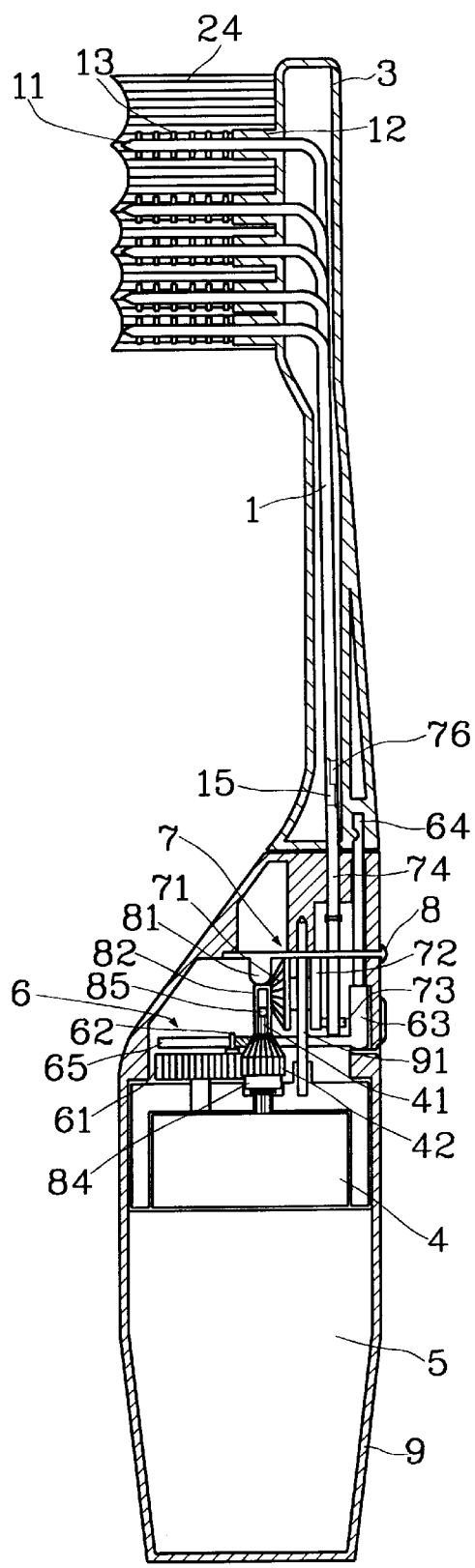
FIGS. 6A and 6B are sectional views of the embodiment shown in FIG. 5, at different operating using states.
Figure 6B:
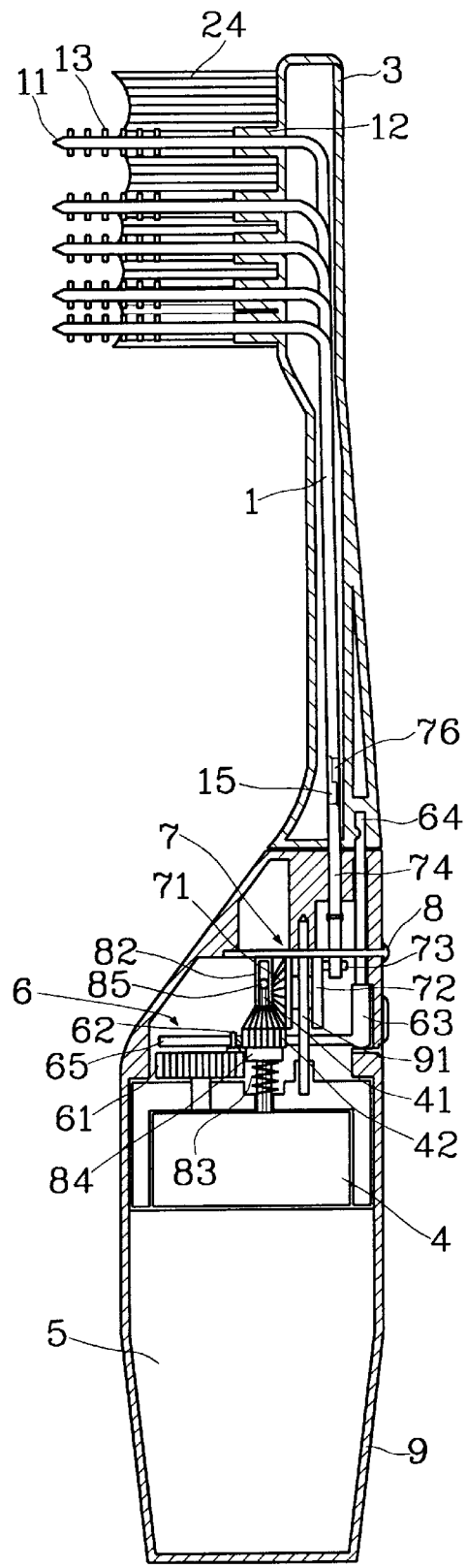

FIGS. 5, 6A and 6B show another embodiment of this invention which is driven by electric power. It includes a movable block head 3, a scraping bristle stem 1, a motor 4, a battery 5, an oscillation means 6, a reciprocal means 7, a switch 8 and a shell 9. The scraping bristle stem 1 is constructed like a tree with a plural number of scraping brushes formed at two sides and a later notch 15 formed on a latch end 17. (shown in FIG. 8). The motor 4 has an output shaft 41 to drive a gear 42 which in turn activates the oscillation means 6 for moving the movable block head 3 rocking left and right about 15° for cleaning teeth. The motor 4 is driven by the battery 5 and is activated by the switch 8. The output shaft 41 may also drive the reciprocal means 7 which will alternately push the scraping bristle 11 outward from the bristle 24 and withdraw the scraping bristle 11 again in the bristles 24 for scraping tartars in the gingiva sulcus.

The motor 4 and battery 5 are fixedly located at a lower portion of the electrical brush. The output shaft 41 is formed in a cross crosssection and is slidably engageable at a front portion thereof with the gear 42 which includes a spur gear and a bevel gear.

Figure 7:
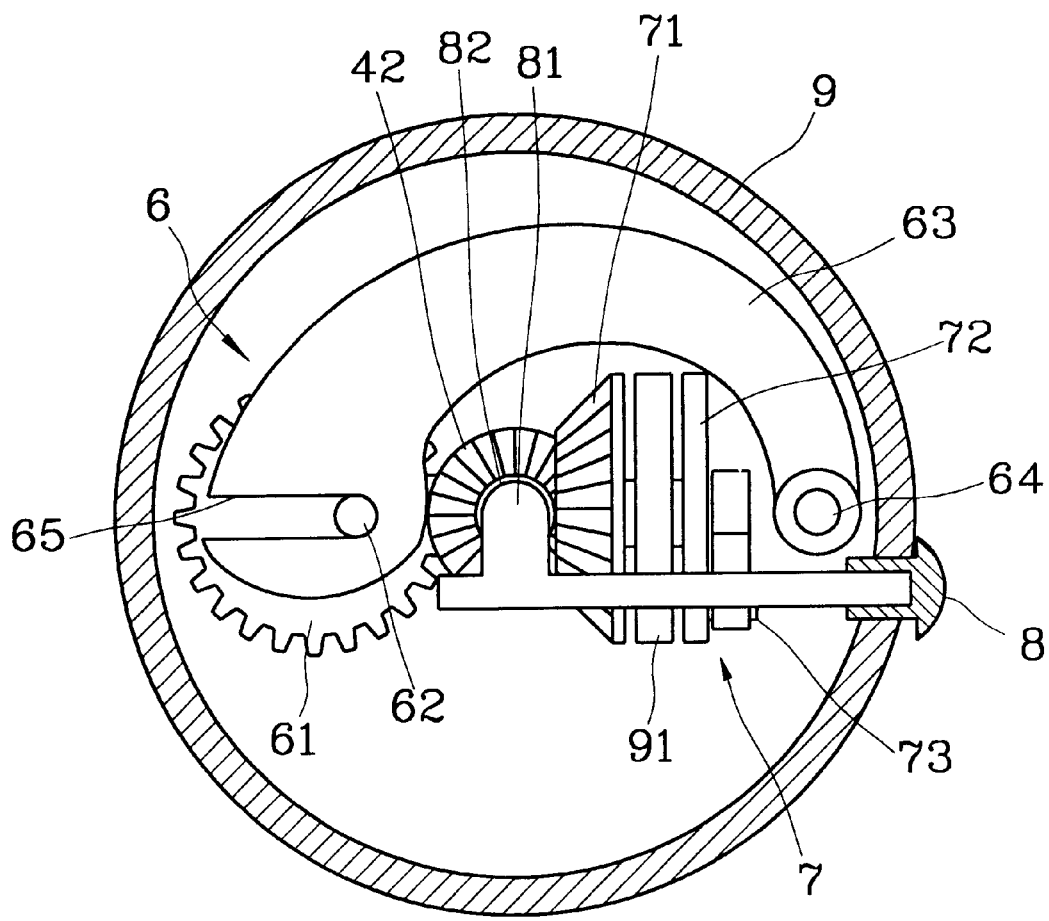
FIG. 7 is a cross sectional view of a switch shown in FIG. 5.

Referring to FIGS. 6A and 7, the switch 8 is mounted on one end of a turnable bar which has a protrusive tongue 81 located at another end. Below the tongue 81, there is a sleeve 82 which has a steel ball 85 located therein. Around the output shaft 41 and below the gear 42, there are a spring 83 and a bearing 84. By turning the switch 8 for 90°, the tongue 81 will press the sleeve 82 downward, the gear 42 will engage with the oscillation means 6. The steel ball 85 will make contact with the bearing 84 for reducing frictional force and motor power loss resulting from the friction.

The oscillation means 6 includes a transmission gear 61 engaged with the gear 42 laterally. The transmission gear 61 has an eccentric stub 62 fixed thereon. The eccentric stub 62 is slidably engaged with a slot 65 formed at one end of a rocking arm 63 which has another end pivotly fixed on a spindle 64 which in turn is engageable with the movable block head 3 of the toothbrush. When the gear 42 rotates and drives the transmission gear 61 to rotate, the eccentric stub 62 will slide in the slot 65 and makes the rocking arm 63 oscillating to and fro, and consequently making the toothbrush oscillating for brushing teeth.

Figure 8:
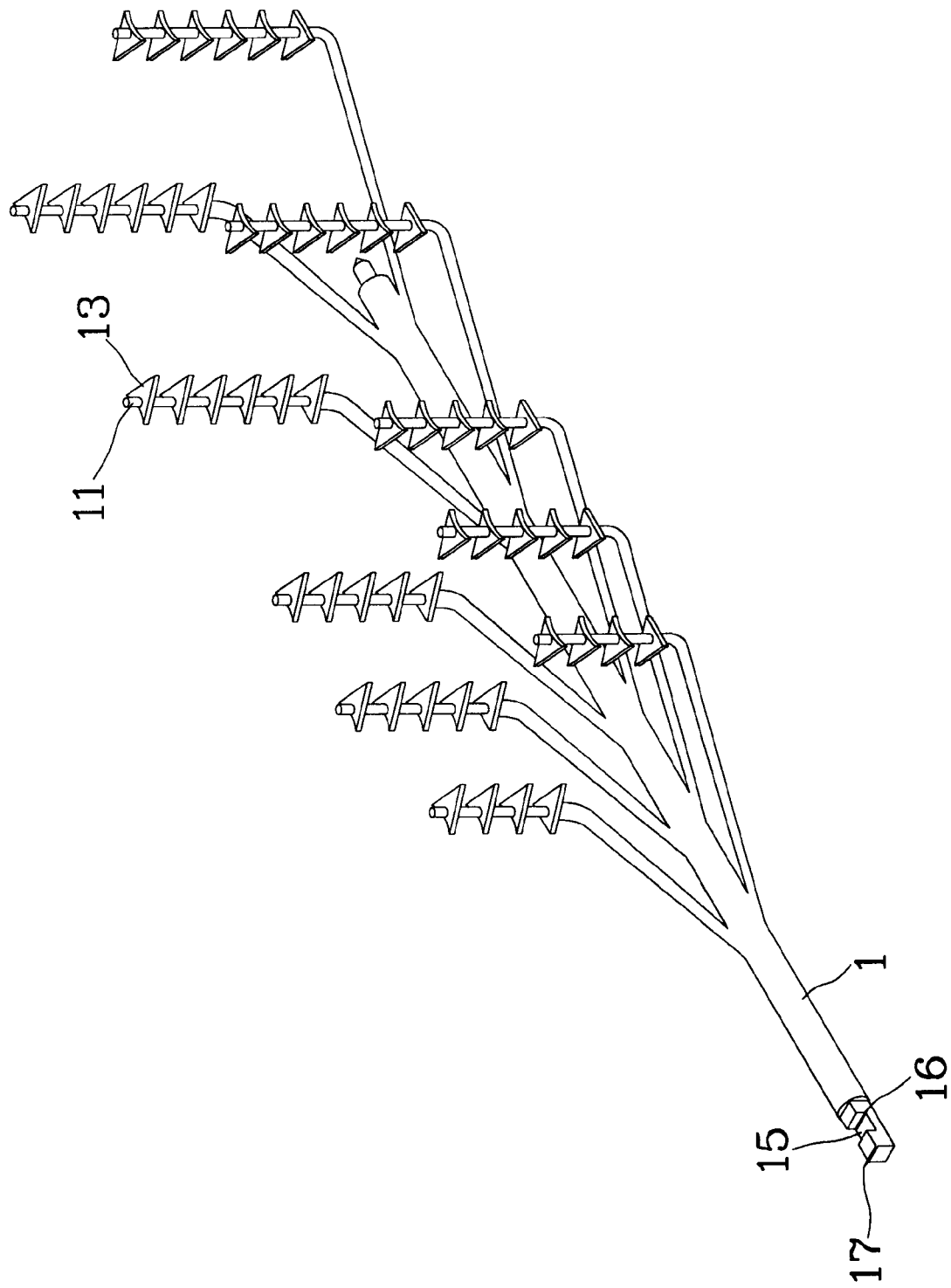
FIG. 8 is a perspective view of gingiva sulcus scraping bristles, shown in FIG. 5, when used in an electrical toothbrush.
Figure 9:
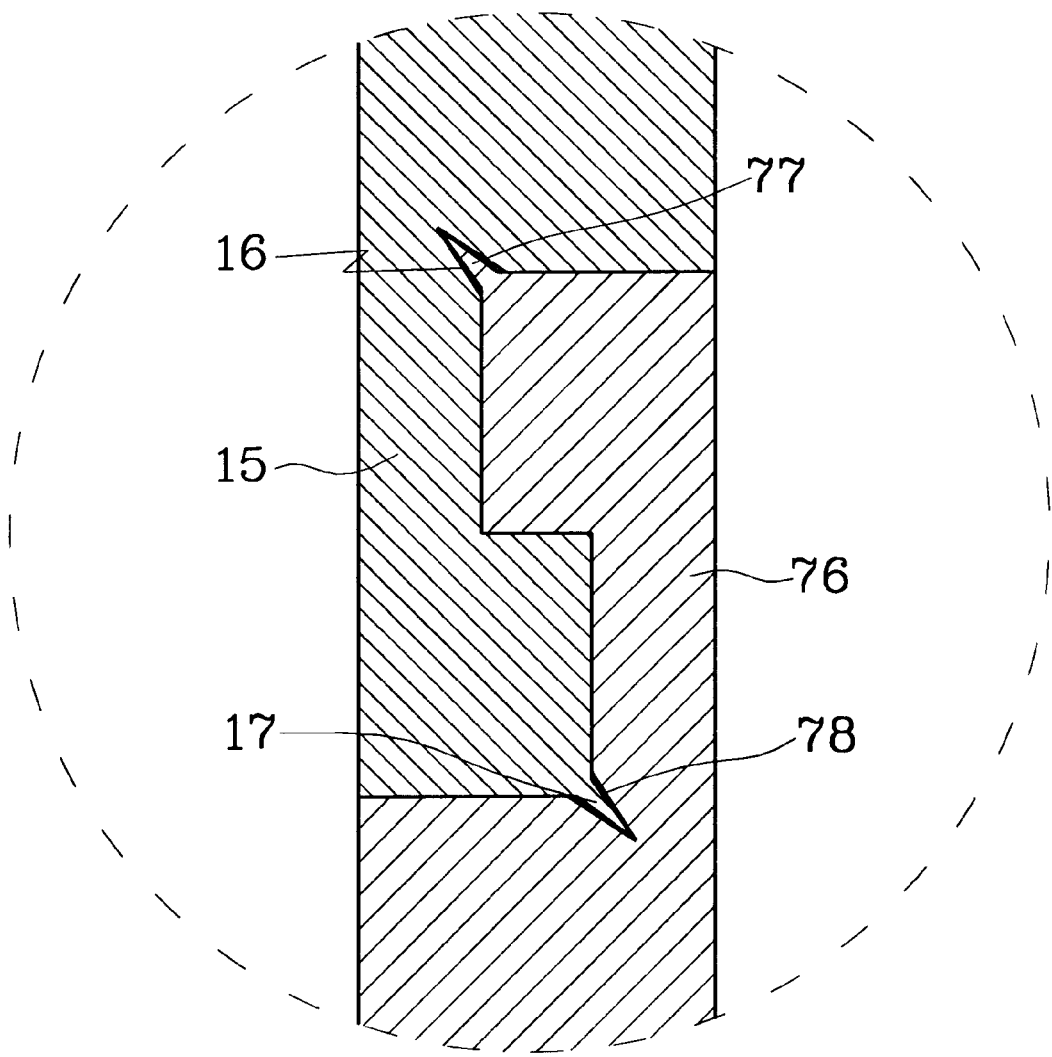
FIG. 9 is a fragmentary sectional view of a latching means between a scraping bristle stem and a linkage bar.

Referring to FIGS. 8 and 9, the scraping bristle stem 1 has a latch end 17 and a latch notch 15 formed nearby. In the latch notch 15, there is a first wedge slot 16. The latch notch 15 and the first wedge slot 16 are engageable securely with a mating second latch notch 76 and a second wedge slot 78 formed on a linkage bar 74.

Referring to FIGS. 5, and 6B, the reciprocal moving means 7 includes a bevel gear 71 engaged normally with the gear 42. The bevel gear 71 has its spindle supported by a frame 91 fixedly mounted on the shell 9. One end of the bevel gear spindle goes through the frame 91 and fixedly attached to a disk 72. There is a stub 73 eccentrically located on the disk 72 and engageable with an aperture 75 located at one end of the linkage bar 74. At an upper portion of the linkage bar 74, the second latch notch 76 and the second wedge slot 78 are provided to engage with the latch notch 15 and the first wedge slot 16 of the bristle stem 1 (also shown in FIG. 9). When in use, turn the switch 8 to make the protrusive tongue 81 at a horizontal position (as shown in FIG. 6B). The spring 83 will push the bearing 84 and the gear 42 upward to engage with the bevel gear 71. When the motor 4 is activated to rotate the gear 42, the bevel gear 71 and disk 72 will be driven to rotate. The eccentric stub 73 will move the linkage bar 74, and consequently the scraping bristle stem 1 up and down reciprocally for scraping tartars in the gingiva sulcus.

According to this invention, the tip profile of the bristle 24 is mating with the dental arch, so that this toothbrush may be precisely positioned upon teeth surface and interdental area to clean teeth and interdental area more effectively by normal up and down toothbrush movement. The scraping bristle may further scrape gingiva sulcus thoroughly and effectively than conventional dental floss. All this can be done single-handedly and neatly. For those who are used to brush teeth transversely, the wave-like tip profile of the bristles still can clean the interdental area effectively. The smooth feeling of this toothbrush will induce people to adopt the correct up and down toothbrushing practice. As every person has unique and different dental arch, this invention may be made in a wide variety of brush form and profile to suit different needs, so that a person can select the one with suitable bristle tip profile and scraping bristle space to meet his or her particularly requirement.

What is claimed is:

1. A toothbrush with inter-gingiva-sulcus scraping bristle, comprising:

a plurality of bristle clusters having a combined bristle top contour that generally mates with the dental arch on a row of teeth to be brushed;

a scraping bristle stem, movable in a block head of the toothbrush, a plurality of scraping bristle branches horizontally branching from the scraping bristle stem, and a plurality of scraping bristles vertically and respectively extending from the scraping bristle branches, each scraping bristle further having a plurality of spaced scraping flakes located thereon, wherein the scraping flakes are made of an elastic material;

a plurality of tubes located in the block head for the scraping bristles to pass therethrough, the tubes are structured to cause the scraping bristles to be moved vertically with respect to the surface of the block head when the scraping bristle stem is moved horizontally; and a moving member for moving the bristle stem horizontally along the block head, so as to allow the scraping bristles to move to and fro in gingiva sulcus and the scraping flakes to scrap off tartars formed on teeth surfaces when the bristle clusters are positioned against the dental arch.

2. The toothbrush according to claim 1, wherein the bristle clusters are arranged in a staggered manner from one another so as to completely cover an area to be brushed.

3. A manually operated toothbrush, comprising:

a plurality of bristle clusters having a combined bristle top contour that generally mates with the dental arch on a row of teeth to be brushed;

a scraping bristle stem, movable in a block head of the toothbrush, and a plurality of scraping bristles extending from the scraping bristle stem, each scraping bristle further having a plurality of spaced scraping flakes located thereon;

a plurality of tubes located in the block head for the scraping bristles to pass therethrough, the tubes are structured to cause the scraping bristles to be moved vertically with respect to the surface of the block head when the scraping bristle stem is moved horizontally, so as to allow the scraping bristles to move to and fro in gingiva sulcus and the scraping flakes to scrap off tartars formed on teeth surfaces when the bristle clusters are positioned against the dental arch;

said manually operated toothbrush further having a block handle which has a pair of lateral slots and a master slot, a master button slidable in the master slot and an elastic member located in the block head engageable with an end of the scraping bristle stem, the scraping bristle stem including two separate stems, wherein each scraping bristle stem has a side button slidably engageable with one of the lateral slots and has another end thereof engageable with the master button.

4. An electrically operated toothbrush, comprising:

a plurality of bristle clusters having a combined bristle top contour that generally mates with the dental arch on a row of teeth to be brushed;

a scraping bristle stem, movable in a block head of the toothbrush, and a plurality of scraping bristles extending from the scraping bristle stem, each scraping bristle further having a plurality of spaced scraping flakes located thereon;

a plurality of tubes located in the block head for the scraping bristles to pass therethrough, the tubes are structured to cause the scraping bristles to be moved vertically with respect to the surface of the block head when the scraping bristle stem is moved horizontally, so as to allow the scraping bristles to move to and fro in gingiva sulcus and the scraping flakes to scrap off tartars formed on teeth surfaces when the bristle clusters are positioned against the dental arch;

said electrically operated toothbrush further having a shell, a movable block head, a motor, a battery, an oscillation means, a reciprocal means and a switch, wherein the scraping bristle stem has a latch means at one end thereof, the motor being driven by the battery, the switch being able to activate a slidable driving gear mounting on a motor shaft to drive the oscillation means to oscillate the block head for brushing teeth or to drive the reciprocal means to extend or retract the scraping bristles in the gingiva sulcus for removing tartars and dental plaque formed therein.

5. The toothbrush according to claim 4, wherein the motor shaft has a cross crosssection engageable with a cross bore formed in the driving gear.

6. The toothbrush according to claim 4, wherein the driving gear includes both spur gear teeth and bevel gear teeth.

7. The toothbrush according to claim 4, wherein the switch is located on the shell and engages with a turnable stem at one end, the turnable stem having another end which has a protrusive tongue engageable with a sleeve located below the tongue, the motor shaft further having a spring and a bearing slidably mounted thereon below the driving gear.

8. The toothbrush according to claim 4, wherein the oscillation means includes a transmission gear engageable with the driving gear laterally, the transmission gear having an eccentric stub on a top thereof, the stub being engageable with a slot in a rocking arm which is located in the shell with a pivot end engaged with the block head for moving the block head oscillatively.

9. The toothbrush according to claim 4, wherein the reciprocal means includes a bevel gear engageable normally with the driving gear, the bevel gear having a spindle which has one end engaged with a disk on which a second eccentric stub is located thereon, the second eccentric stub being engageable with one end of a linkage bar which has a latching end engageable with the latch means of the scraping bristle stem.

10. The toothbrush according to claim 9, wherein the latching end and the latch means both include a latching notch and a wedge slot for providing engagement between the linkage bar and the scraping bristle stem.

* * * * *